US00PP17066P3

(12) United States Plant Patent
Shibamichi

(10) Patent No.: US PP17,066 P3
(45) Date of Patent: Aug. 29, 2006

(54) **PLANT VARIETY *DAVIDIA INVOLUCRATA* NAMED 'AYA NISHIKI'**

(50) Latin Name: *Davidia involucrata*
Varietal Denomination: Aya Nishiki

(75) Inventor: Akira Shibamichi, Kawaguchi (JP)

(73) Assignee: Hines Nurseries, Inc., Irvine, CA (US)

( * ) Notice: Subject to any disclaimer, the term of this patent is extended or adjusted under 35 U.S.C. 154(b) by 0 days.

(21) Appl. No.: 10/984,264

(22) Filed: Nov. 8, 2004

(65) Prior Publication Data

US 2006/0101549 P1 May 11, 2006

(51) Int. Cl.
*A01H 5/00* (2006.01)

(52) U.S. Cl. ..... Plt./216

(58) Field of Classification Search ..... Plt./216
See application file for complete search history.

*Primary Examiner*—Kent Bell
*Assistant Examiner*—Annette H Para
(74) *Attorney, Agent, or Firm*—Christie, Parker & Hale, LLP

(57) ABSTRACT

A new plant variety of *Davidia involucrata* distinguished from its parents and all other varieties of *Davidia involucrata* of which I am aware by the broadly cream variegated leaf margins on spring foliage and mottled variegation on secondary foliage in summer and fall.

2 Drawing Sheets

Botanical classification: *Davidia involucrata* (Baill.)
Varietal name: 'Aya Nishiki'.

BACKGROUND OF THE INVENTION

The present invention relates to a new and distinct variety of *Davidia involucrata,* which was developed in a controlled breeding program in Kawaguchi City, Japan, by the originator Mr. Akira Shibamichi. The varietal denomination of the new variety is 'Aya Nishiki'.

The genus *Davidia* is included in the family Davidiaceae, which comprises one genus and one species originating in Western China. *Davidia involucrata* is uncommon in its native habit of Western China. It generally has a habit of a 20 meter tall deciduous tree with a dominant central leader, branches thick, glabrous. Leaf color is green, depending on light intensity and cultural conditions. Leaves are generally broadly ovate, 8 to 24 cms long, cordate at base, dentate, glossy and glabrous above, densely gray tomentose beneath. Petioles are 4 to 5 cms long, red, flowers are about 2 cm wide, surrounded by 2 opposite, uneven sized, 8 to 16 cm long, pendulous, yellowish white involucral leaves. Plant blooms May to June on older, mature specimens often more than 20 years in age. Fruits are ellipsoid, about 2.5 cms long.

SUMMARY OF THE INVENTION

The new variety was discovered as an open pollinated seedling in a controlled planting of *Davidia involucrata.* The new variety differs from its parents in having broadly margined creamy white variegation on new foliage, followed by foliage with blue green, white and green mottled foliage. Asexual reproduction of the new variety in Kawaguchi City, Japan by grafting has confirmed that the distinctive characteristics of the new variety are stable and reproduced true to type in successive generations of asexual propagation.

COMPARISON WITH PARENTS

'Aya Nishiki' is distinguished from its parents and all other varieties of *Davidia involucrata* of which I am aware, including the specific variety, *Davidia involucrata* var. *Vilmoriniana* (not patented) by the broadly cream variegated leaf margins on spring foliage and mottled variegation on secondary foliage in summer and fall.

BRIEF DESCRIPTION OF ILLUSTRATIONS

The accompanying illustrations show a specimen of the new cultivar in a photo illustration as true to color as is reasonably possible to make in an illustration of this character.

DETAILED DESCRIPTION OF THE NEW VARIETY

Figure 1:
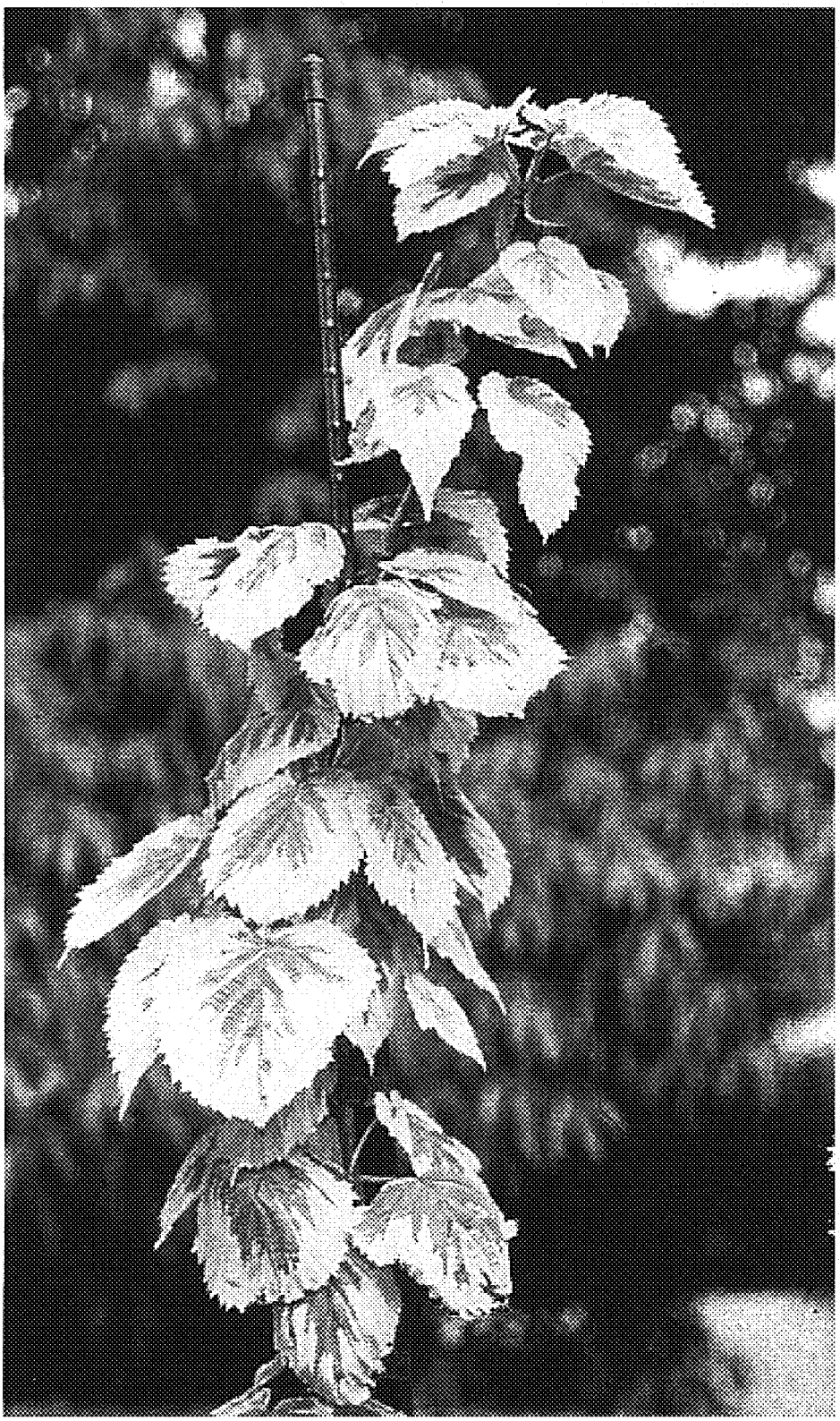
FIG. 1 illustrates spring foliage of the new variety
Figure 2:
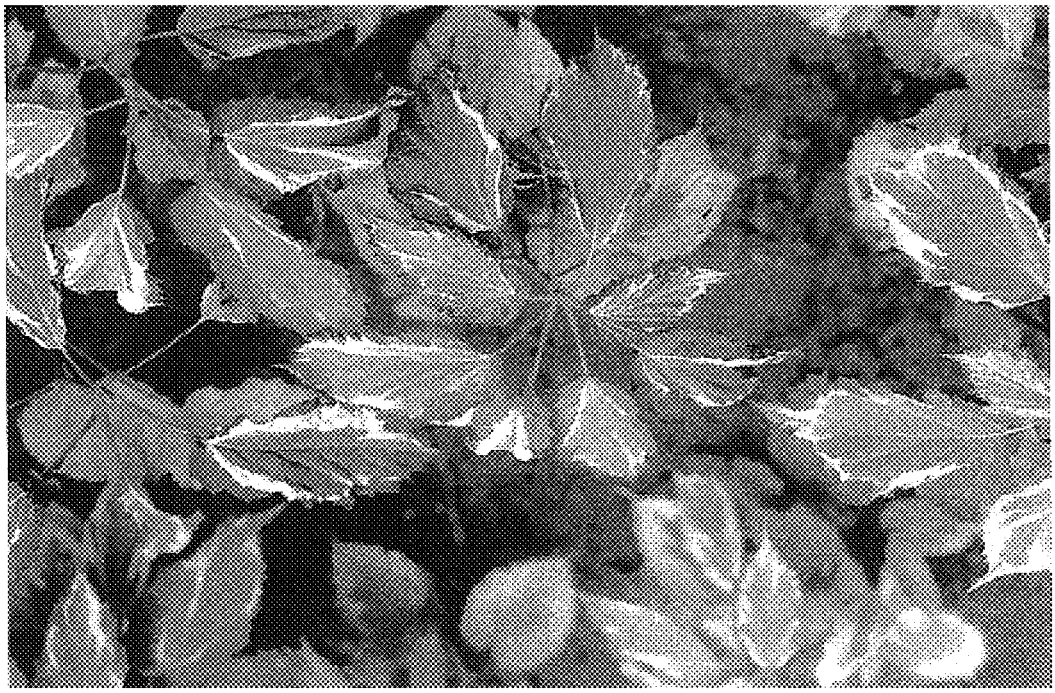
FIG. 2 illustrates the summer foliage of the new variety

'Aya Nishiki' has not been observed under all possible environmental, cultural and light conditions. The following observations and descriptions are of plants grown in Kawaguchi City, Japan and Vacaville, Calif. In this description, color references are to The Royal Horticultural Society Colour Chart (2002) and terminology used in the color descriptions herein refers to plate numbers in this color chart. Phenotypic expression may vary with light intensity, cultural and environmental conditions.

Classification:

*Botanical.*—*Davidia involucrata* (Baill.).

*Parentage.*—Mother Plant: *Davidia involucrata* (unnamed, unpatented). Father Plant: *Davidia involucrata* (unnamed, unpatented).

*Propagation.*—Grafting.

Plant:

*Typical size.*—20 meters tall.

*Observed size.*—1.5 meters tall.

*Habit.*—Upright, pyramidal.

Branches:

*Lateral branches.*—8 to 10.

*Size.*—Diameter: Base 10 to 20 mm; apex 2 to 3 mm. Color: Near Grey-Brown Group N199A. Texture: Glabrous. Color of New Shoots: Near Greyed Green Group 1 97B.

Leaf:

*Shape.*—Broadly ovate. Base: Cordate to dentate. Apex: Acuminate.

*Leaf size.*—8 to 14 cms long and 5 to 8 cms wide.

*Arrangement.*—Alternate.

*Margin.*—Entire.

*Texture/substance.*—Glossy and glabrous above and densely tomentose beneath.

*Description of variegation on mature and young foliage.*—Initial growth in spring exhibits broadly marginal variegation against a green background. Subsequent foliage growth in summer exhibits mottled green and burgundy margins with blue green colored central foliage.

*Young foliage variegated margins.*—Upper side: Near Yellow-Green Group 150 D with occasional coloration of Red Purple Group 68C–D. Under side: Near Yellow-Green Group 150 B.

*Width of variegation.*—0.5 cm–2.5 cms.

*Young foliage central.*—Upper side: Near Green Group 133 C with occasional Blue Green Group 121 C. Underside: Blue Green Group 121 C.

*Mature foliage margins.*—Upper side: Near Green Group 133 C often with Greyed-Purple Group 186 B–C. Under side: Near Green Group 133 C. Width of margin: 2–3 mms.

*Transition zone between margins and central coloration.*—Color: Near White Group 155 A. Width: 1–2 mms.

*Mature foliage central.*—Upper side: Near Green Group 133C–D. Under side: Near Green Group 1 33D.

*Venation pattern.*—Upper Surface: Impressed.

*Petioles.*—Size: 7.5 cms long; 1 to 2 mm wide. Coloration: Near Red-Purple Group 59A. Texture: Smooth.

*Internodes.*—3 to 8 cms.

*Hardiness.*—USDA Zone 5 (−20° F. to −10° F.).

*Vigor.*—Moderate.

*Pests/diseases.*—None noted.

Inflorescence: None yet observed.

I claim:

1. A new and distinct *Davidia involucrata* plant of the variety substantially as shown and described.

* * * * *